United States Patent
Tran

(10) Patent No.: US 7,290,978 B2
(45) Date of Patent: Nov. 6, 2007

(54) PHOTOMASK FLIPPER AND SINGLE DIRECTION INSPECTION DEVICE FOR DUAL SIDE PHOTOMASK INSPECTION

(75) Inventor: Daniel Tran, San Jose, CA (US)

(73) Assignee: n&k Technology Inc., Santa Clara, CA (US)

( * ) Notice: Subject to any disclaimer, the term of this patent is extended or adjusted under 35 U.S.C. 154(b) by 365 days.

(21) Appl. No.: 10/865,741

(22) Filed: Jun. 9, 2004

(65) Prior Publication Data

US 2006/0018748 A1    Jan. 26, 2006

(51) Int. Cl.
*B07C 1/18* (2006.01)
*B21B 39/24* (2006.01)

(52) U.S. Cl. ............... 414/763; 414/764; 414/771; 414/783; 901/31

(58) Field of Classification Search ............. 414/758, 414/759, 760, 761, 763; 901/31, 33, 34; 356/244, 426
See application file for complete search history.

(56) References Cited

U.S. PATENT DOCUMENTS

| | | | | |
|---|---|---|---|---|
| 3,508,806 A | * | 4/1970 | Hall | 359/393 |
| 4,042,122 A | * | 8/1977 | Espy et al. | 414/728 |
| 4,998,232 A | | 3/1991 | Methlie et al. | 369/30.43 |
| 5,010,536 A | | 4/1991 | Wanger et al. | 369/30.48 |
| 5,056,073 A | | 10/1991 | Fitzgerald et al. | 369/30.73 |
| 5,059,772 A | | 10/1991 | Younglove | 235/383 |
| 5,101,387 A | | 3/1992 | Wanger et al. | 369/30.45 |
| 5,184,336 A | | 2/1993 | Wanger et al. | 369/30.34 |
| 5,421,889 A | * | 6/1995 | Pollock et al. | 118/719 |
| 5,644,559 A | | 7/1997 | Cristie, Jr. et al. | 369/30.43 |
| 5,819,651 A | * | 10/1998 | Zepic et al. | 101/127.1 |
| 6,142,725 A | * | 11/2000 | Crorey | 414/753.1 |
| 6,310,685 B1 | * | 10/2001 | Baan et al. | 356/244 |
| 6,606,154 B1 | * | 8/2003 | Oda | 356/244 |
| 2003/0190225 A1 | * | 10/2003 | Marincic et al. | 414/758 |

* cited by examiner

*Primary Examiner*—Patrick Mackey
*Assistant Examiner*—Gregory W Adams
(74) *Attorney, Agent, or Firm*—Johannes Schneeberger

(57) ABSTRACT

A flipper for rotating and positioning a photomask in two flip orientations includes a flip unit rotatably held in a base. The flip unit includes a flip frame in which clamps are preferably spring loaded guided such that the clamps are oppositely and laterally displaceable between engaged positions and parking positions. A stepper motor rotates the flip unit between two flip orientations and positions the flip unit such that opposite inspection sides of the work piece are alternately oriented with respect to a single inspection direction. The flipper may be placed on or adjacent to a stage system of an inspection device. A robotically actuated effector may access the flipper for loading and unloading the work piece. In combination with an effector operating without lift motion, the clamps may feature wedge lift faces to lift the work piece off the effector during their actuation into engaged position.

10 Claims, 7 Drawing Sheets

PHOTOMASK FLIPPER AND SINGLE DIRECTION INSPECTION DEVICE FOR DUAL SIDE PHOTOMASK INSPECTION

FIELD OF INVENTION

The present invention relates to work piece flippers for dual side inspection from a single inspection direction. Particularly, the present invention relates to a photomask flipper and a single head inspection device for dual side non destructive photomask inspection.

BACKGROUND OF INVENTION

Continuous advancement in fabrication techniques involving photomasks requires ever increasing inspection thoroughness. In the prior art, photomasks have been mainly inspected from a single side. Having inspection devices capable of inspecting a photomask from both sides significantly increases inspection possibilities. Inspecting photomasks from both sides in an efficient and space saving fashion requires a specifically configured mechanical device. Therefore, there exists a need for a photomask flipper simple and reliable in design and configured for assembly within an inspection device such as a semiconductor metrology tool. The present invention addresses this need.

SUMMARY OF INVENTION

A flipper for rotating and positioning a flat work piece such as a photomask includes a flip unit rotatably held in a base. The flip unit includes a flip frame in which clamps are preferably spring loaded guided such that the clamps are oppositely and laterally displaceable between engaged positions and parking positions. A motor in the preferred configuration of a well known stepper motor rotates the flip unit between two flip orientations and positions the flip unit such that opposite inspection sides of the work piece are alternately oriented with respect to a single inspection direction.

The clamps are actuated by actuators that are preferably attached to the base actuating the clamps via access faces that are in operational alignment with the actuators during at least one of the two flip orientations. In such preferred assembly configuration, the actuators push the clamps against their spring load between the clamps' parking positions and engaged positions. To hold the clamps in engaged positions, latches are positioned on the flip frame and engage with corresponding latch couplers of the clamps. Once the clamps are latched in, the clamps may fixedly hold in engaged position the work piece with respect to the flip frame independently of the actuators action. The fixed work piece may be freely rotated. To return the clamps into their park positions, the actuator may push onto the clamps and trigger release them from their latches during one of the two flip orientations. The preferred placing of the actuators on the base provides for a compact and simple configuration of the flip unit.

The flipper may be placed on a stage system of an inspection device or may be placed adjacent to the stage system. The inspection device such as a spectrometer may perform inspection from a single inspection with respect to which the two flip orientations are aligned. A robotically actuated effector may access the flipper for loading and unloading the work piece. In combination with an effector operating without lift motion, the clamps may feature wedge lift faces to lift the work piece off the effector during their actuation into engaged position.

DETAILED DESCRIPTION

Figure 1:
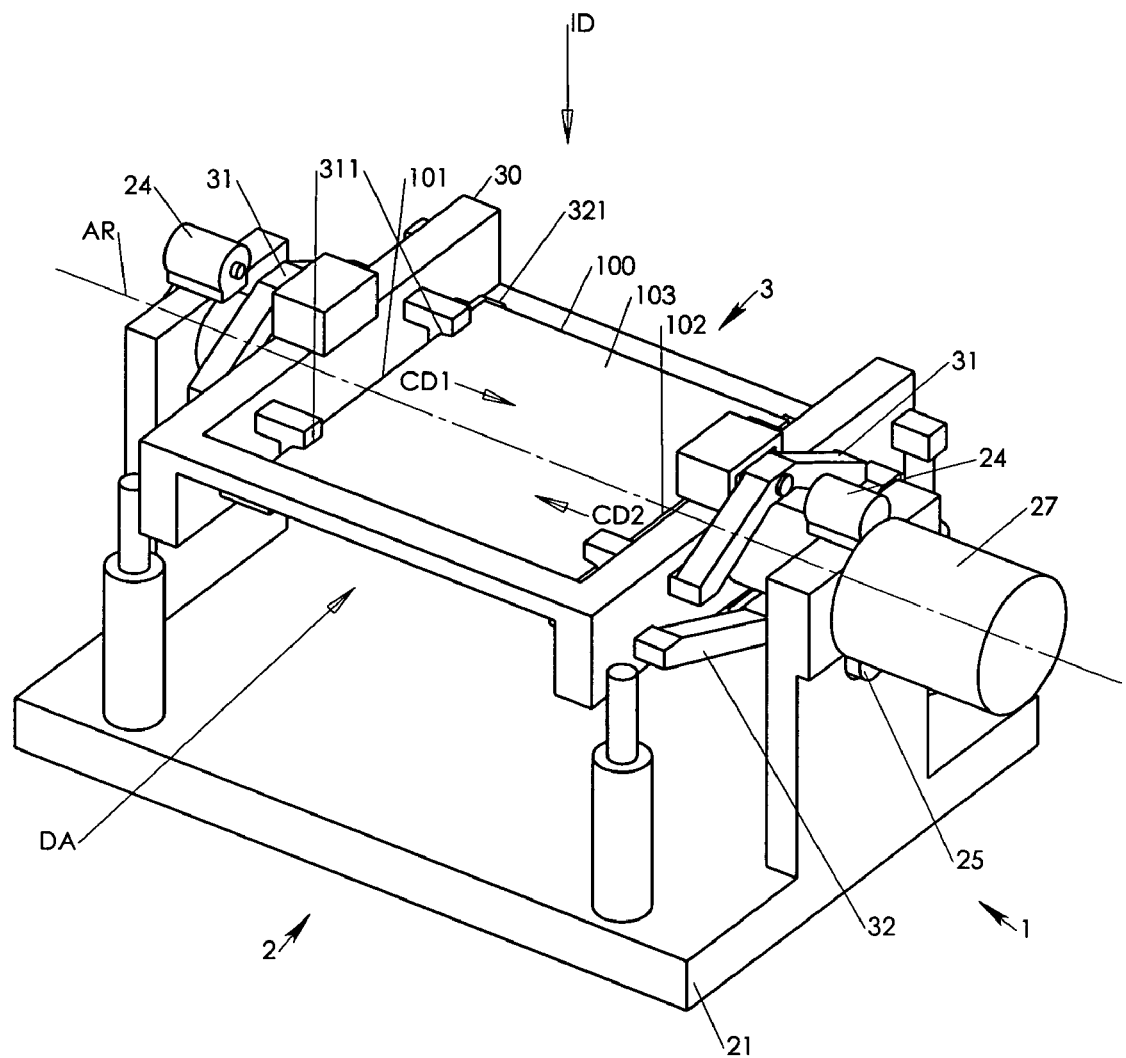
FIG. 1 shows a first perspective view of an exemplary photomask flipper in a first flip orientation.
Figure 2:
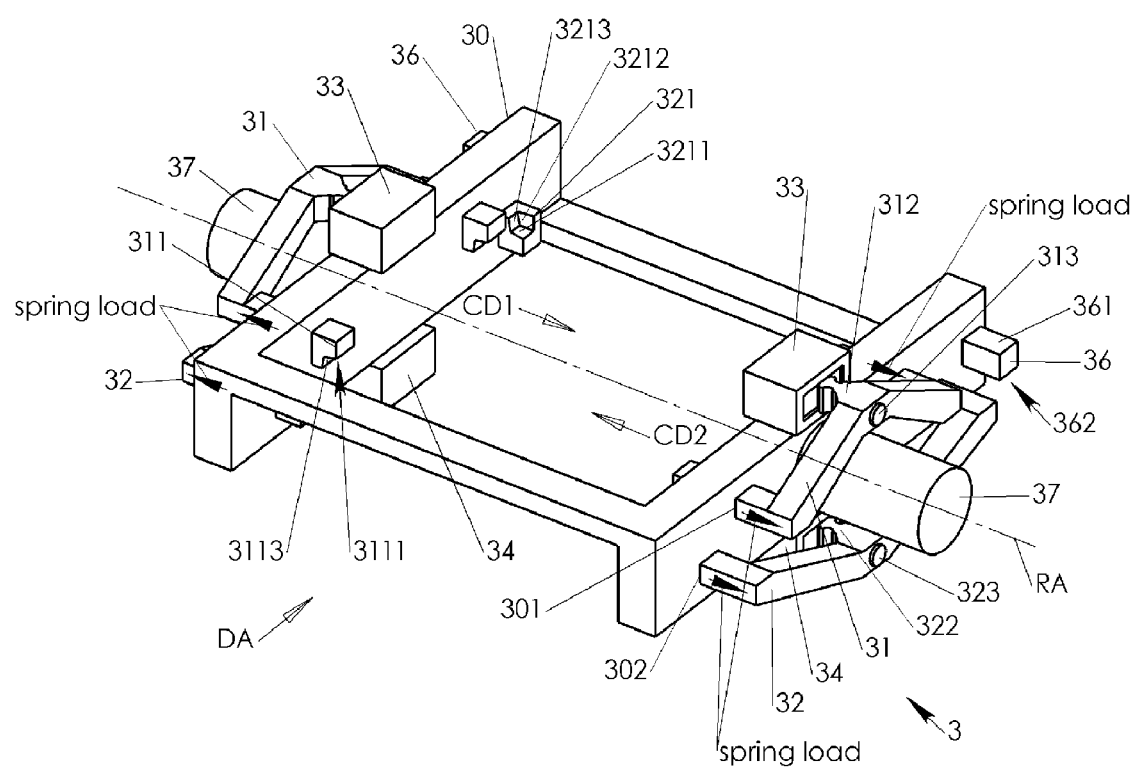
FIG. 2 is the first perspective view of an exemplary flip unit of the photomask flipper of FIG. 1.
Figure 3:
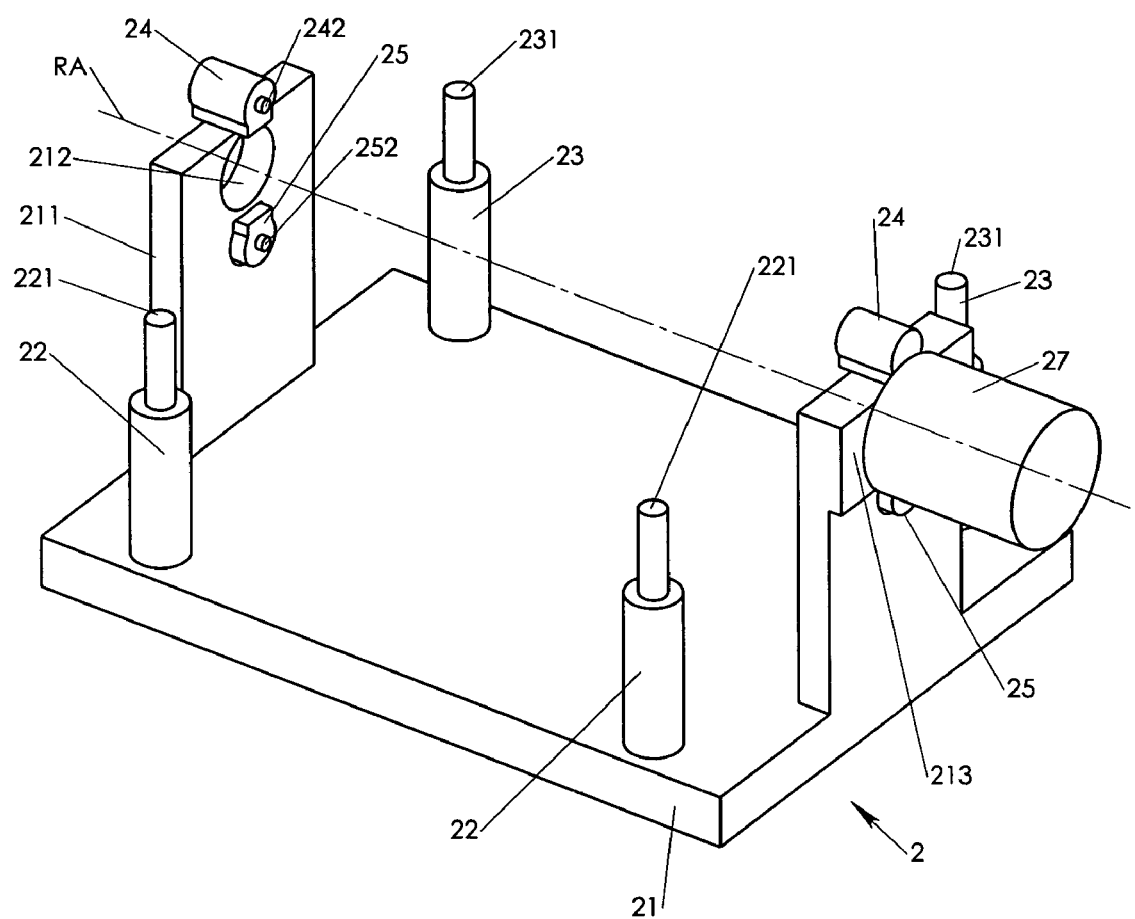
FIG. 3 is the first perspective view of an exemplary base unit of the photomask flipper of FIG. 1.
Figure 4:
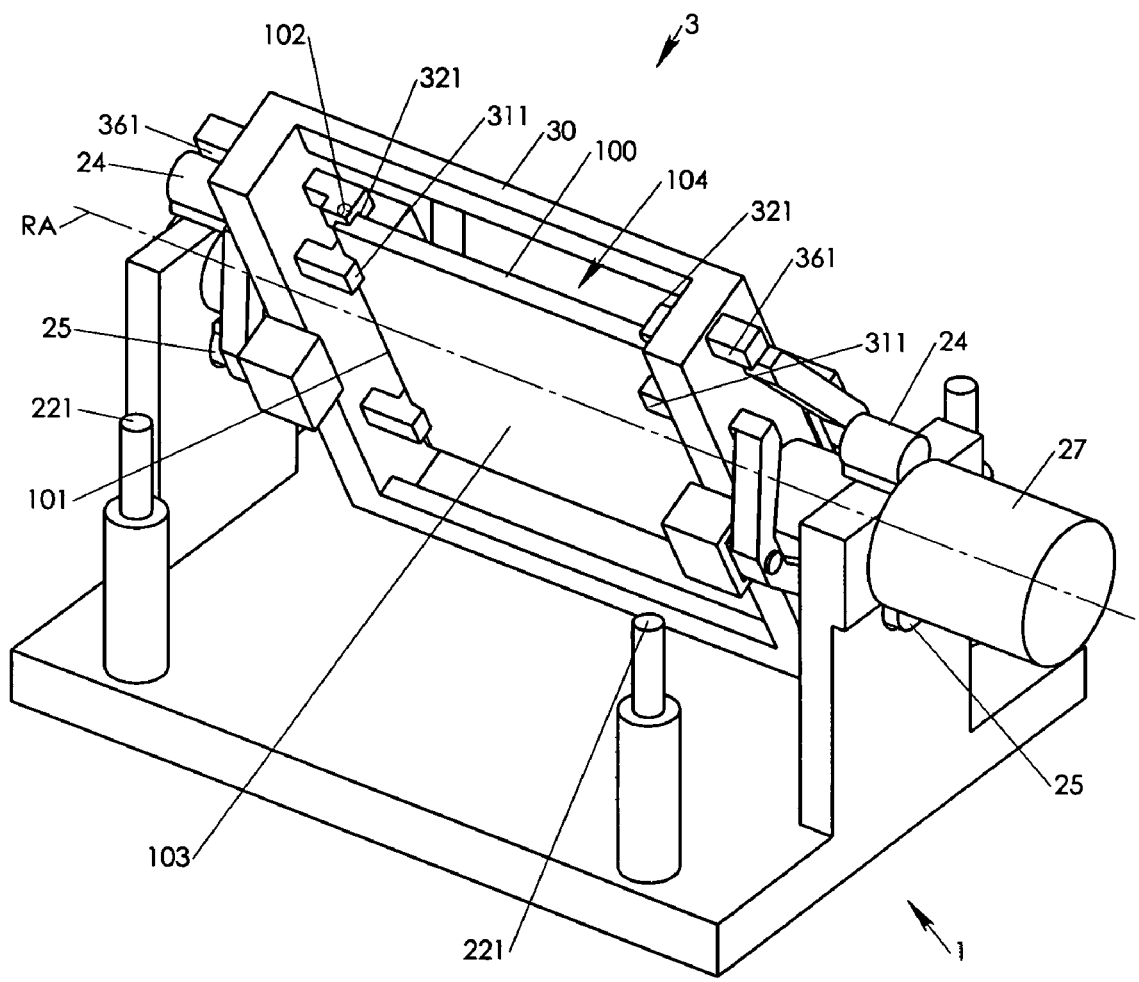
FIG. 4 is the first perspective view of the photomask flipper of FIG. 1 with the flip unit rotating between the first flip orientation and a second flip orientation.
Figure 5:
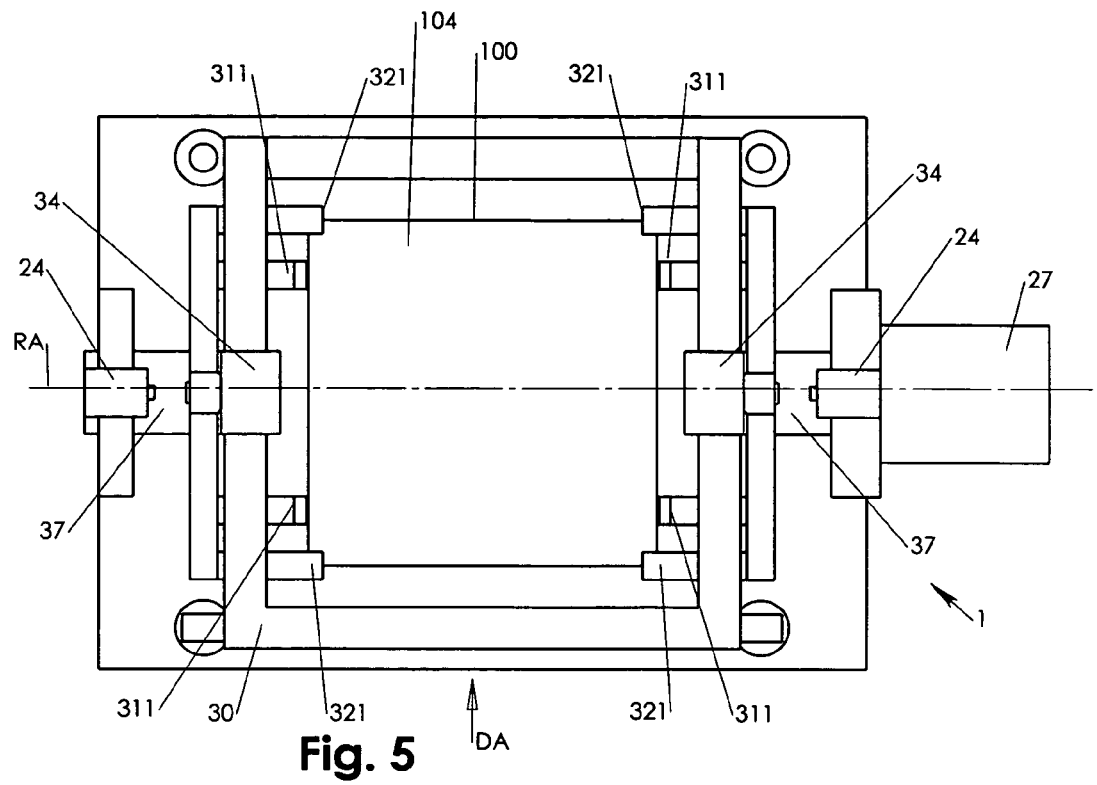
FIG. 5 is a top view of the photomask flipper of FIG. 1 in the second flip orientation.
Figure 6:
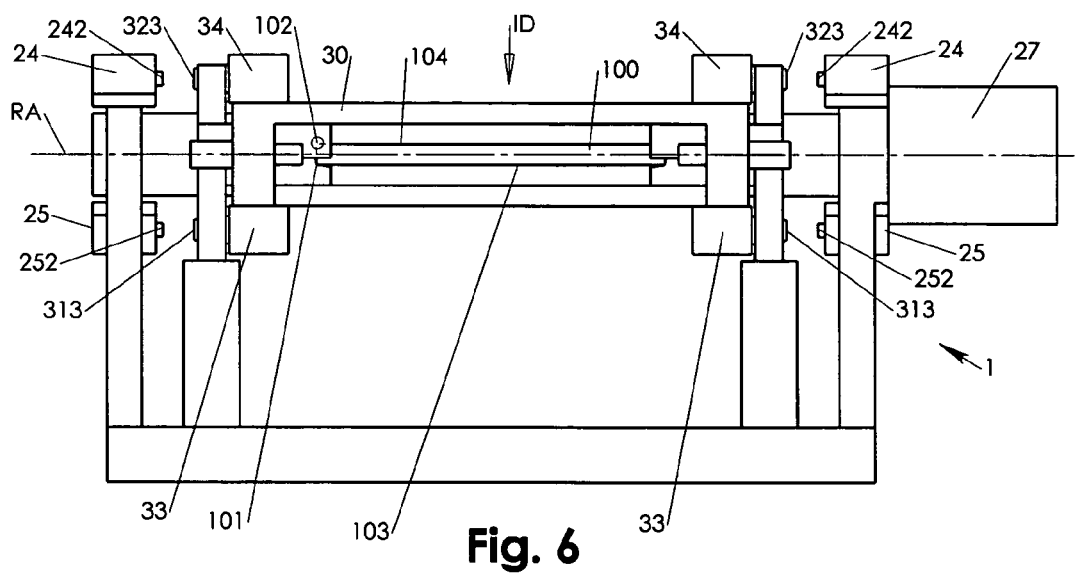
FIG. 6 is a front view of the photomask flipper of FIG. 1 in the second flip orientation.

Referring to FIGS. 1-6, a flipper 1 features a base unit 2 rotatably holding a flip unit 3. The flip unit 3 features a flip frame 30 and at least two oppositely and laterally displaceable clamps 31, 32. The clamps 31, 32 are guided via guides 301, 302 in the flip frame 30. Each clamp 31, 32 has one or more respective claws 311, 321 for engaging with a form feature 101, 102 of a flat work piece 100 while the clamps 31, 32 are in an engaged position. In the preferred case of the work piece 100 being a photomask, a first form feature 101 may be an edge at a first inspection side 103 of the photomask and a second form feature 102 may be a corner at a second inspection side 104 of the photomask. Second form features 102 are shown in dashed lines since they are obstructed by claws 321 in the Figures. In engaged position of both clamps 31, 32, the flat work piece 100 is held by the claws 311, 321 substantially fixed with respect to the flip frame 30.

The clamps 31, 32 are actuated by actuators 24 and optionally by additional actuators 25 along clamp directions CD1, CD2 between their engaged position and a parking position. A motor 27 in the preferred configuration of a well known stepper motor rotates the flip unit 3 around the flip axis AR and alternately positions the flip unit 3 in both flip orientations such that alternately the two opposite inspection sides 103, 104 are oriented with respect to a single inspection direction ID. The motor 27 is preferably attached to the base 2.

In the case of actuators 24 and eventually 25 being attached to the base 2, the flip unit 3 may further include latches 33, 34 in a number equal to the clamps 31, 32 such that latch couplers 312, 322 of the respective clamps 31, 32 may be latched in and trigger released from their respective latches 33, 34. The actuators 24, 25 are attached to the base 2 such that each of the actuators 24, 25 accesses an access face 313, 323 of one of the clamps 31, 32 for latching in and trigger releasing the clamps 31, 32 during at least one of first and second flip orientation. The clamps 31, 32 may be spring loaded guided for exerting a contact pressure via their access faces 313, 323 onto the respective actuators 24, 25.

Assembling the actuators 24, 25 together with supply cables and/or supply lines on the bearing posts 211 of the base 2, provides for simple and compact design of the flip unit 3. The latches 33, 34 may be prefabricated and commercially available without particular need for accuracy. The actuators 24, 25 may also be mounted on the flip unit 3 in which case the use of latches 33, 34 may be optional, since the latches' 33, 34 continuous holding function may be provided by the actuators 24, 25. The actuators 24, 25 may be electrically and/or pneumatically operated.

The flip unit 3 may feature well known position sensors for detecting proper position of the involved clamps 31, 32 and/or the flat work piece 100. The sensors provide signals to a well known control unit for logically controlling the operation of the flip unit 3 in the context of a flipping operation as may be well appreciated by anyone skilled in the art. To transmit the control signals from the sensors and supply voltage to the sensors, a well known slip ring may be assembled on the flip unit's 3 shaft 37. Via the slip ring also actuators 24, 25 may be electrically accessed in case the actuators 25, 24 are mounted in electrically operated configuration on the flip frame 30. In case of actuators 25, 24 being mounted on the flip unit 3, the actuators 24, 25 may continuously hold the clamps 31, 32 in either or both parking and engaged position thus eliminating latches 33, 34 and latch couplers 312, 322.

Each clamp 31, 32 has at least one but preferably two respective claws 311, 321. The claws' 321 positions with respect to the work piece 100 are defined in the engaged position in dependence on the order in which the claws are brought into engaged position. In a first engaging sequence where the claws 321 are initially brought into engaged position, the claws 321 position is defined by the interaction between stop faces 3213 and respective form features 102 and the claws' 311 positions is defined in the engaged position by the interaction between wedge faces 3111 and respective form features 101. In a second engaging sequence where the claws 311 are initially brought into engaged position, the claws 311 position is defined by the interaction between stop faces 3113 and respective form features 101 and the claws' 321 positions is defined in the engaged position by the interaction between wedge faces 3211 and respective form features 101.

In case of latches 33, 34 being employed for holding the clamps 31, 32 in engaged positions, the claws 311, 321 are preferably spring loaded moveable in clamp direction CD1, CD2 relative to their respective latch couplers 312, 322. In that way, the claws' 311, 321 positions are independent of the latches' 33, 34 latching precision.

First and second flip orientations are calibrated by the interaction between a rotation stopper 36 of the flip unit 3 and positioners 22, 23 of the base unit 2. The positioners 22, 23 have positioning faces 221, 231 that alternately contact with rotation stop faces 361, 362 of the rotation stopper 36. In FIG. 1, the first flip orientation is shown and in FIGS. 5, 6 the second flip orientation is shown. The position faces 221, 231 may be adjustable in height for a precise calibration of both flip orientations. The position faces 221, 231 may also incorporate well known sensors recognizing the contacting condition of a respective rotation stop face 361, 362. The motor 27 may be controlled in conjunction with the position face sensors' output to exert a certain holding torque onto the flip unit 3 and forcing a continuous contact between position faces 221, 231 and respective rotation stop faces 361, 362. In that fashion, precise orientation of the first and second inspection sides with respect to the single inspection direction ID at the respective first and second flip orientation is ascertained.

The base unit 2 is preferably structurally configured with a base plate 21 combined with two bearing posts 211, which in turn feature a bearing seat 212 and a motor flange 213. The bearing posts 211 eventually hold the actuators 24, 25 in case of latches 33, 34 being employed on the flip unit 3.

The clamps 31, 32 may be combined with actuators 24, 25 and in conjunction with an effector's 131 (see FIGS. 7, 8) functionality to operate in accordance with the first and/or second engaging sequence. To describe such combination in more detail, clamps 31, 32, actuators 24, 25, actuation faces 242, 252, claws 311, 321, latches 33, 34, clamp accesses 313, 323 and latch couplers 312, 322 may be distinctly defined in the following as primary clamps 31 and secondary clamps 32, primary actuators 24 and secondary actuators 25, primary actuation faces 242 and secondary actuation faces 252, primary claws 311 and secondary claws 321, primary latches 33 and secondary latches 34, primary clamp accesses 313 and secondary clamp accesses 323, and primary latch couplers 312 and secondary latch couplers 322.

In a first embodiment in which the effector 131 provides a lift motion for lowering and lifting the flat work piece 100, the clamps 31/32 being below the inserted work piece 100 may remain in engaged position during lowering and lifting of the work piece 100 by the effector 131. After the work piece 100 is lowered onto the below clamps 31/32, the above clamps 31/32 may be brought into engaged position thereby fixing the work piece 100 with respect to the flip frame 30. This corresponds for the first flip orientation with the first engaging sequence and for the second flip orientation with the second engaging sequence. In the first embodiment, only clamps 31/32 being in the above position need to the actuated, which necessitates solely actuators 24 mounted on the base unit 2. In case of an actuator mounting location on the flip unit 3, actuators 24, 25 are employed.

In a second embodiment in which the effector 131 does not provide lift motion, clamps 31, 32 both are actuated in the above and below position relative to the work piece 100. In this embodiment, actuators 24 and 25 are provided irrespective their mounting location either on the base unit 2 or the flip unit 3.

During work piece 100 loading and unloading in the first embodiment, the flip unit 3 may be preferably initially brought into first flip orientation where the secondary claws 321 with their wedge centering faces 3212 are below the loaded work piece 100. The frame 30 is configured to provide access for the effector 131 and the work piece 100 in loading direction DA. Primary claws 311 are in parking position and secondary claws 321 are in engaged position while the work piece 100 is inserted within the boundaries of the flip frame 30 and lowered down with its second form features 102 onto the secondary claws 321. Wedge centering faces 3212 provide an alignment of the work piece 100 in loading direction DA. Stop faces 3213 provide alignment of work piece 100 in clamp direction CD1/CD2. The effector 131 is further lowered such that the weight of the work piece 100 is fully transferred on the secondary clamps 321 and sufficiently spaced from the effector 131 for the uninhibited retraction of the effector 131. Once the work piece 100 is in full contact with the secondary claws 321, the primary clamps 31 are actuated until the primary latch couplers 312 latch in the primary latches 33. The wedge faces 3111 are thereby resiliently brought into contact with the first form features 101 and the work piece 100 is fixed with respect to the flip frame 30. This condition may be recognized in a well known fashion by sensors as well as the full retraction of the effector 131 outside the range of the flip unit 3. In a following step, the motor 27 may initiate a rotation of the flip unit 3 until the rotation stop faces 362 come in contact with the positioning faces 221. Then, the secondary clamps 32 may be trigger released by the actuators 24 and spring loaded retract into parking position. The effector 131 may again advance into unloading position, lift the work piece 100 off the primary claws 311 such that the work piece 100 fully rests on the effector 131 and both work piece 100 and effector 131 may retract from the flipper 1. After unloading, the secondary clamps 32 may be brought back into engaged position before the flip unit 3 is rotated back into first flip orientation where the primary clamps 31 are brought again into park position before a work piece 100 flipping operation may be repeated.

Loading and unloading of the work piece 100 in the second embodiment is similar to that of the first embodiment except that the below claws 311/321 are in brought into parking position prior to insertion of the effector 131 during loading and after insertion of the effector 131 during unloading. The below wedge lift faces 3111/3211 provide during actuation into engaged position a lift motion to lift the work piece off the effector 131 and a lowering motion to lower the work piece 100 onto the effector 131 while actuated into parking position. Where the lift motion is provided by the clamps 31/32 actuation a work piece handling mechanism 13 may have only two axis motion capability for operating the effector 131.

Since during unloading no substantial lateral force is encountered, the primary claws 311 may be configured without centering faces. The primary claws 311 may consequently be positioned in an inward offset with respect to the secondary claws 321, which again allows for a configuration of the wedge centering faces 3212 and stop faces 3113, 3213 irrespective of the work piece's 100 height. Wedge centering faces 3212 are configured for carrying the work piece's 100 weight during rotation where the work piece 100 is rotated through its vertical orientation. Wedge centering faces 3212 are also configured for a sufficient centering of the work piece 100 with respect to the loading direction DA while maintaining sufficient spacing to avoid locking in of the work piece 100 in between opposite wedge centering faces 3212 as may be well appreciated by anyone skilled in the art.

Figure 7:
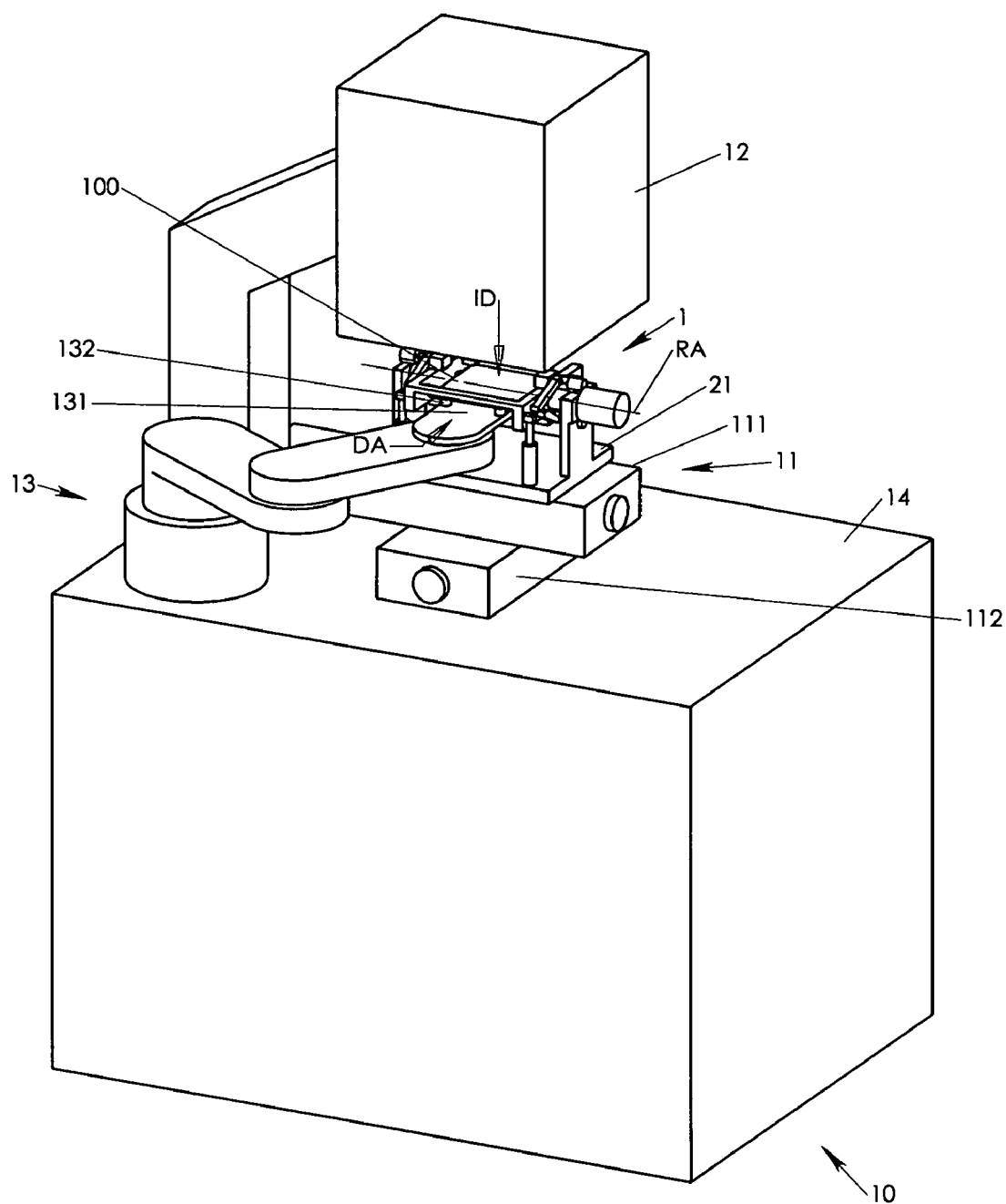
FIG. 7 is a second perspective view of an inspection device with the photomask flipper of FIG. 1 positioned on a stage system.
Figure 8:
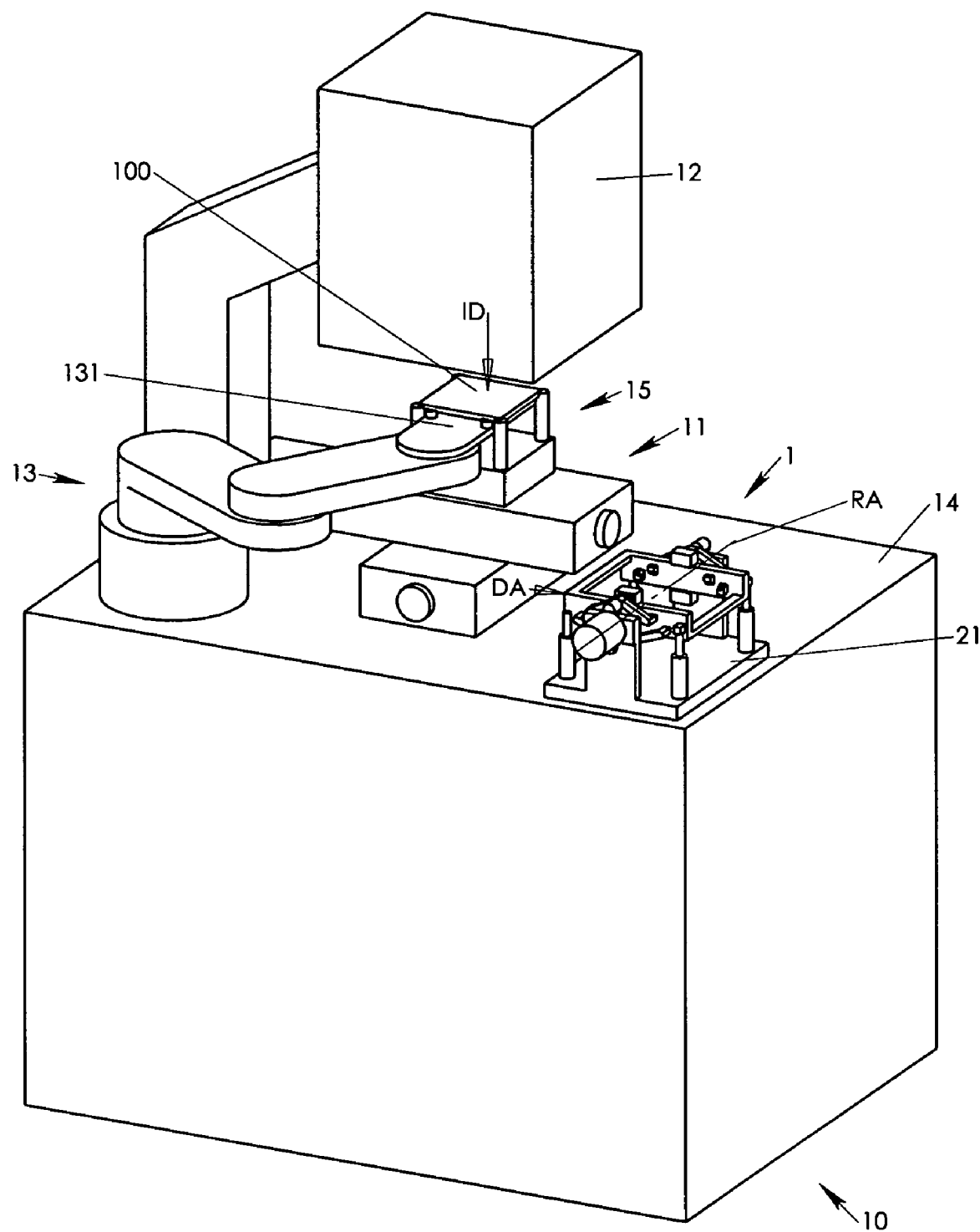
FIG. 8 is the second perspective view of an inspection device with the photomask flipper of FIG. 1 positioned adjacent the stage system.

Referring to FIGS. 7, 8, the flipper 1 and the work piece handling mechanism 13 may be part of a testing device 10 for non destructively testing a flat work piece 100 in an inspection position along a single inspection direction ID. Such testing device 10 is preferably a spectrometer. The flipper 1 may be attached with its base plate 21 on a stage system 11 or on a device base 13. The flipper 1 is accessible along the loading direction DA by the effector 131 of the handling mechanism 13. The handling mechanism 13 may provide three axis motion of the effector 131 in combination with the first embodiment of the flipper 1. The handling mechanism 13 may provide two axis motion of the effector 131 without lift motion in combination with the second embodiment of the flipper 1. The handling mechanism 13 may be assembled on the device base 13 or may be combined with the testing device 10 in any other well known fashion. The handling mechanism 13 may further be attached to and/or part of the stage system 11. The stage system 11 may include an X-stage 111 and a Y-stage 112. The effector 131 may have work piece holding studs 132.

The combination of handling mechanism 13 and work piece flipper 1 provides for an automatic inspection of the work piece 100 on both inspection sides 103, 104 from a single inspection direction ID of a testing head 12. In the case illustrated in FIG. 7 where the flipper 1 is attached to the stage system 11, the flipper 1 provides also the inspection position of the work piece 100. The circumferential configuration of the flip unit 3 with respect to the fixed work piece 100 and the ability to retract the above clamps 31/32 during both flip orientations provides free access to the inspection sides 103/104 along the inspection direction ID.

In case illustrated in FIG. 8 where the flipper 1 is placed adjacent the stage system 11, a chuck 15 may be employed on the stage system 11 for positioning the work piece 100 in the inspection position. The chuck 15 may provide lifting and lowering functionality in combination with a second embodiment flipper 1 and a two motion axis handling mechanism 13. The work piece 100 may be transferred between the chuck 15 and the flipper 1 for alternately orienting the inspection sides 103, 104 towards the inspection direction ID.

Accordingly, the scope of the invention described in the specification above is set forth by the following claims and their legal equivalent:

What is claimed is:

1. A flipper for rotating between and alternately positioning at a first flip orientation and a second flip orientation a flat work piece such that alternately two opposite inspection sides of said flat work piece are oriented with respect to a single inspection direction, said work piece flipper comprising:
   a. a flip unit including:
      I. a flip frame;
      II. at least two primary latches and at least two secondary latches combined with said flip frame;
      III. at least two oppositely and laterally displace able primary clamps, each primary clamp having:
         1. a primary claw for engaging with a first form feature of said work piece during a primary engaged position;
         2. a primary latch coupler for latching in said primary latch during said primary engaged position;
         3. a primary clamp access for peripherally actuating said each primary clamp between a park position and said primary engaged position and for triggering a release of said primary latch;
      IV. at least two oppositely and laterally displace able secondary clamps, each secondary clamp having:
         1. a secondary claw for engaging with a second form feature of said work piece during a secondary engaged position;
         2. a secondary latch coupler for latching in said secondary latch during said secondary engaged position;
         3. a secondary clamp access for peripherally actuating said each secondary clamp between a park position and said secondary engaged position and for triggering a release of said secondary latch;
      wherein said primary clamps and said secondary clamps are spring loaded guided in said flip frame such that during simultaneous said primary engaged position and said secondary engaged position said work piece is held substantially fixed with respect to said flip frame;
      wherein during said simultaneous engaged positions said latches hold said clamps against said spring load;

b. a base unit rotatably holding said flip unit, said base unit including:
   I. at least two initial actuators positioned such that an initial actuation face of each of said initial actuators faces said primary clamp access for said peripheryal actuation of one of said at least two primary clamps during said first flip orientation and such that said initial actuation faces face said secondary clamp access for said peripheral actuation of one of said at least two secondary clamps during said second flip orientation;
   II. at least two follow actuators positioned such that a follow actuation face of each of said follow actuators faces said secondary clamp access for said peripheryal actuation of one of said at least two secondary clamps during said first flip orientation and such that said follow actuation faces face said primary clamp access for said peripheryal actuation of one of said at least two primary clamps during said second flip orientation;
   III. a motor for rotating said flip unit with respect to said base;
   wherein said peripheral actuation provides for said park position, said engaged position and said latch release triggering; and
   wherein said primary claws have wedge lift faces for inducing a lift motion onto said work piece while said primary clamps are actuated into said primary engaged position.

2. The flipper of claim 1, wherein said primary claw is a corner claw having three position faces corresponding to said first form feature in the configuration of a corner.

3. The flipper of claim 1, wherein said secondary claw is an edge claw having two position faces corresponding to said second form feature in the configuration of an edge.

4. The flipper of claim 1, wherein at least one of said primary claw and said secondary claw is spring loaded moveable in clamp direction relative to a respective one of said primary latch coupler and said secondary latch coupler.

5. The flipper of claim 1, wherein at least one of said primary claw and said secondary claw features a stop face interacting with a respective one of said first form feature and said second form feature during said engaged position such that said claw is positioned along a clamp direction of said clamp.

6. The flipper of claim 1, wherein at least one of said primary claw and said secondary claw features a wedge lift face for inducing a lifting motion on said work piece while said at least one claw is actuated into said engaged position.

7. The flipper of claim 1, wherein at least one of said primary claw and said secondary claw features a wedge centering face for inducing a centering motion on said work piece while said at least one claw is actuated into said engaged position.

8. The flipper of claim 1, wherein at least one of said primary claw and said secondary claw features a wedge clamp face for fixing said work piece with respect to said flip frame during said engaged position.

9. The flipper of claim 1, wherein said work piece is a photo mask.

10. The flipper of claim 1 being part of a testing device for non destructively testing a flat work piece in an inspection position along a single inspection direction such that each of said two opposite inspection sides are alternately oriented with respect to said single inspection direction during said first flip orientation and said second flip orientation.

* * * * *